(12) United States Patent
Rivera

(10) Patent No.: US 10,315,017 B2
(45) Date of Patent: Jun. 11, 2019

(54) INCREMENTAL INFLATION TOOL FOR EXTRACTION BALLOONS

(71) Applicant: Cook Medical Technologies LLC, Bloomington, IN (US)

(72) Inventor: Stephanie Rivera, Burlington, NC (US)

(73) Assignee: Cook Medical Technologies LLC, Bloomington, IN (US)

(*) Notice: Subject to any disclaimer, the term of this patent is extended or adjusted under 35 U.S.C. 154(b) by 460 days.

(21) Appl. No.: 14/991,291

(22) Filed: Jan. 8, 2016

(65) Prior Publication Data

US 2016/0213897 A1 Jul. 28, 2016

Related U.S. Application Data

(60) Provisional application No. 62/108,170, filed on Jan. 27, 2015.

(51) Int. Cl.
*A61M 25/10* (2013.01)
*A61B 17/22* (2006.01)
*A61B 90/00* (2016.01)

(52) U.S. Cl.
CPC . *A61M 25/10187* (2013.11); *A61B 17/22032* (2013.01); *A61M 25/10182* (2013.11); *A61B 2017/22062* (2013.01); *A61B 2090/063* (2016.02); *A61M 25/104* (2013.01)

(58) Field of Classification Search
CPC .............. A61M 29/00; A61M 25/10; A61M 25/10187; A61M 25/10182; A61M 29/02; A61B 2017/22062; A61B 2017/00557
See application file for complete search history.

(56) References Cited

U.S. PATENT DOCUMENTS

2010/0204707 A1* 8/2010 Tanaka .................... A61M 1/04
606/108
2013/0165903 A1* 6/2013 Webler .............. A61M 25/1002
604/509

* cited by examiner

*Primary Examiner* — Vi X Nguyen
(74) *Attorney, Agent, or Firm* — Brinks Gilson & Lione

(57) ABSTRACT

Inflation systems and methods for inflating a balloon member are provided. The inflation system includes an inflation tool. The inflation tool includes a first component having a first arm where the first arm extends longitudinally along an axis of movement of the first component. The first arm includes a first and a second positioning member, the first positioning member is longitudinally spaced apart from the second positioning member. The first component is adapted to advance distally for inflation of the balloon member. Each positioning member corresponds to an inflation increment for the balloon member.

15 Claims, 5 Drawing Sheets

US 10,315,017 B2

INCREMENTAL INFLATION TOOL FOR EXTRACTION BALLOONS

RELATED APPLICATIONS

This application claims the benefit of U.S. Provisional Application No. 62/108,170, filed Jan. 27, 2015, which is incorporated by reference herein in its entirety.

FIELD OF THE INVENTION

The present invention relates to medical devices and in particular to an inflation tool for use with balloons.

BACKGROUND OF THE INVENTION

During endoscopic retrograde cholangiopancreatography (ERCP) procedures in which an extraction balloon is being used, a syringe is attached to the hub connected to the inflation lumen. This syringe is used to inflate the extraction balloon to the size necessary, as determined by the clinician, to remove the obstruction. The outer diameter of the inflated balloon typically corresponds with the inner diameter of the duct being swept. Because of the variation in the ductal anatomy, there is not a typical inner diameter for the ducts, for example the ducts within the biliary system, especially when the ducts are compromised with obstructions and strictures.

Currently, manufactures of extraction balloons provide syringes which enable the users to inflate the balloons to specific inflated diameters. Two methods of controlling the inflation volume are typically used. One method uses a hole drilled through the wall of the syringe at a precise location. The location of the hole only allows injection of a controlled volume of air into the balloon. The second method uses protrusions on the inside of the syringe barrel at a precise location to prevent the syringe plunger from travelling the full length of the syringe barrel so that a controlled volume of air is injected in to the balloon. Each type of syringe also includes markings along the syringe barrel to indicate where the plunger must be moved in order to obtain the labeled balloon inflation diameter.

The current syringe devices used for inflating the balloons include at most four predetermined markings. Size constraints on the markings, for example to provide clear visibility and variation in the location of the marking due to dimensional tolerances, limit the number of markings that can be provided as well as the accuracy of the markings on the syringe barrel.

What is needed in the art is a device and a method for allowing incremental inflation of a balloon to allow the clinician to size the balloon to the patient's specific anatomy, allow a greater number of accurate sizes and for repletion of inflation of the balloon to a specific outer diameter.

BRIEF SUMMARY

Accordingly, it is an object of the present invention to provide a device and a method having features that resolve or improve on the above-described current devices.

Inflation systems for inflating a balloon member are provided. The inflation system includes an inflation tool. The inflation tool includes a first component having a first arm where the first arm extends longitudinally along an axis of movement of the first component. The first arm includes a first and a second positioning member, the first positioning member is longitudinally spaced apart from the second positioning member. The first component is adapted to advance distally for inflation of the balloon member. Each positioning member corresponds to an inflation increment for the balloon member.

In another aspect, an inflation system for inflating a balloon member is provided. The inflation system includes an inflation device and an inflation tool. The inflation device includes a syringe having a barrel and a plunger portion where the inflation device is operably connected to the balloon member. The inflation tool includes a first component having a first arm, the first arm extending longitudinally along an axis of movement of the first component. The first arm includes a first positioning member and a second positioning member, the first positioning member longitudinally spaced apart from the second positioning member. The first component is connectable to the plunger portion and is adapted to advance distally with the plunger portion relative to the barrel for inflation of the balloon member. Each positioning member corresponds to an inflation increment for the balloon member.

Methods for inflating a balloon member are provided. The method includes positioning a balloon member at a site. The balloon member is inflatable to a first inflated diameter and a second inflated diameter that is different than the first inflated diameter. The balloon member is operably connected to an inflation device having an inflation tool connected to the inflation device, the inflation tool includes a first component connected to a plunger portion of the inflation device. The first component includes a first arm, the first arm extending longitudinally along an axis of movement of the first component, the first arm including a first positioning member and a second positioning member, the first positioning member longitudinally spaced apart from the second positioning member. The method further includes advancing the plunger portion and the first component distally relative to the barrel portion so that the first positioning member is engaged and the balloon member is inflated to the first inflated diameter and advancing the plunger portion and the first component distally relative to the barrel portion so that the second positioning member is engaged and the balloon member is inflated to the second inflated diameter.

DETAILED DESCRIPTION

Figure 1:
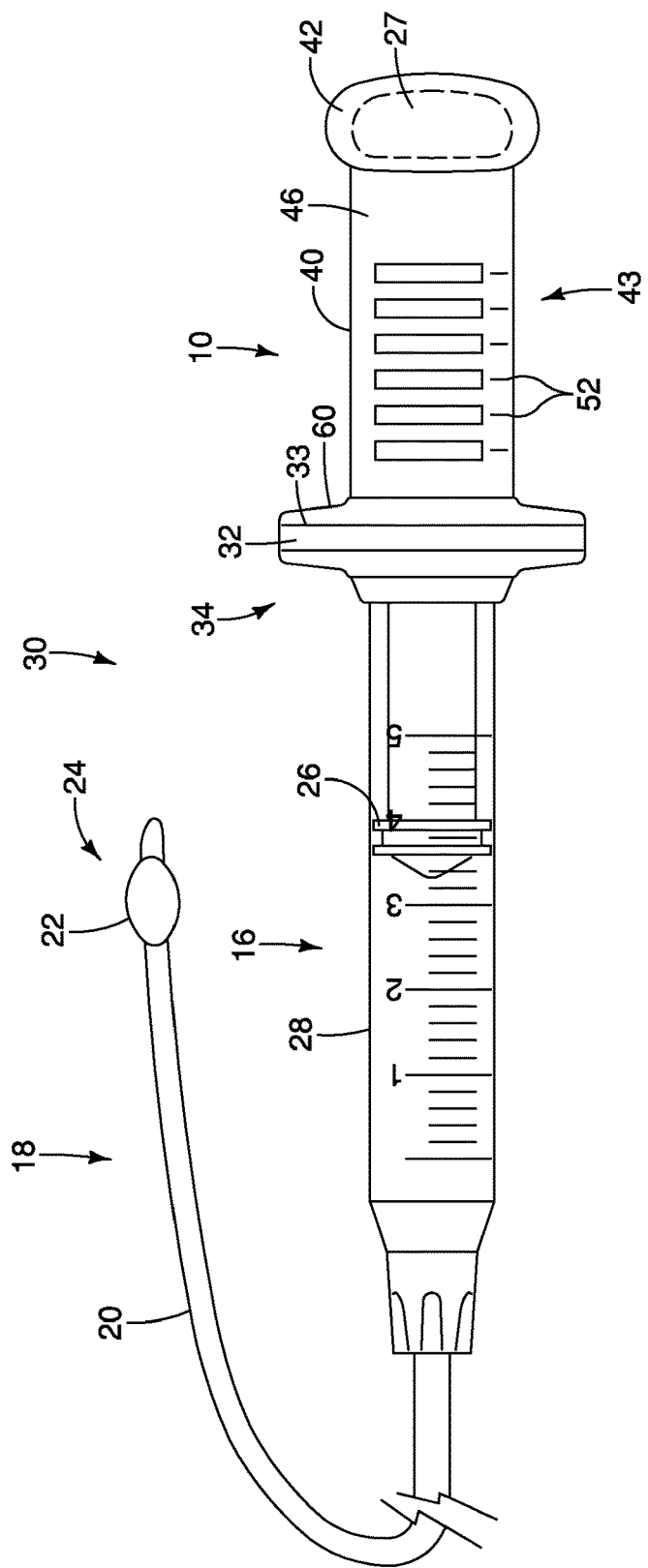
FIG. 1 is a side view of an inflation system in accordance with an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician handling an inflation system with reference to a patient. Hence the term "distal" means the portion of the inflation system that is farthest from the physician and the term "proximal" means the portion of the inflation system that is nearest to the physician.

FIG. 1 illustrates an embodiment of an inflation tool 10 in accordance with the present invention. The inflation tool 10 is shown connected to a syringe 16 and a balloon catheter 18 that includes a shaft 20 and a balloon member 22 operably connected to a distal portion 24 of the balloon catheter 18 that together form an inflation system 30. The balloon member 22 is made of a compliant material such as latex, silicone, or another suitable elastomeric material that can allow the balloon to assume a range of diameters The inflation tool 10 includes a first component 40. In some embodiments, the inflation tool 10 includes a second component 60 as shown in FIG. 1. The first component 40 may be operably connectable to a plunger portion 26 of the syringe 16. A proximal end portion 42 of the first component 40 connects with a proximal end 27 of the plunger portion 26 so that the first component 40 is movable with the plunger portion 26. Both the first component 40 and the plunger portion 26 move relative to a barrel 28 of the syringe 26. The second component 60 may be operably connectable to a flange 32 on a proximal portion 34 of the barrel 28 of the syringe 16. The first component 40 moves longitudinally relative to the second component 60.

Figure 2A:
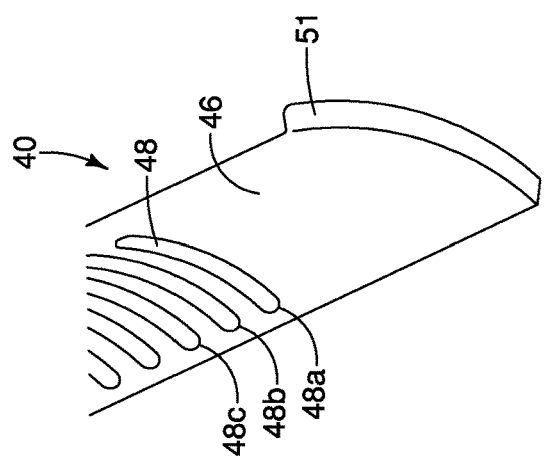
FIG. 2A is an enlarged view of a portion of the first component shown in FIG. 2.
Figure 2:
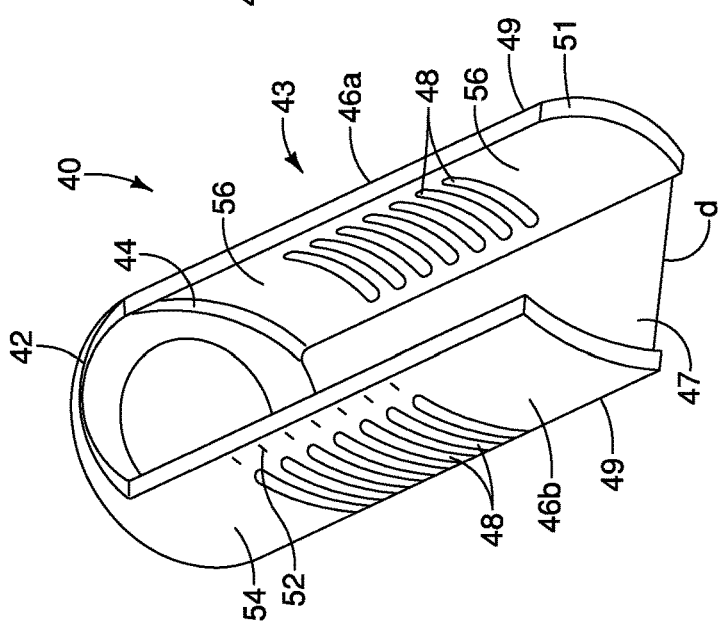
FIG. 2 is a perspective view of an embodiment of a first component of an inflation tool.
Figure 6:
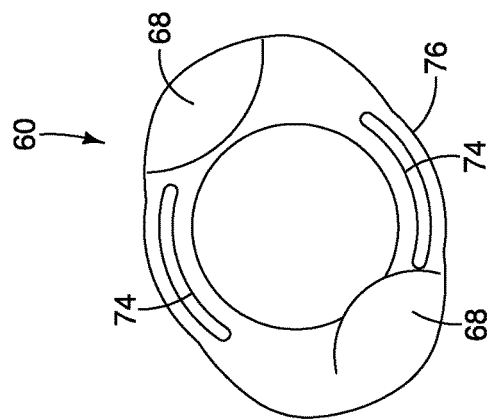
FIG. 6 is a bottom view of the second component shown in FIG. 4.
Figure 5:
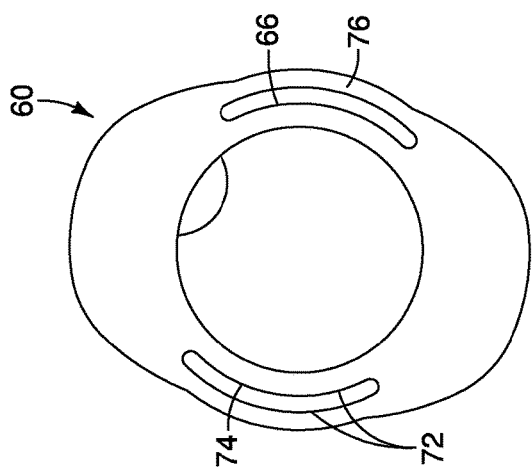
FIG. 5 is top view of the second component shown in FIG. 4.

FIG. 2 illustrates an embodiment of the first component 40 of the inflation tool 10. The first component 40 includes the proximal end portion 42 that may be sized and shaped to fit over the proximal end 27 of the plunger portion 26 so that the proximal end portion 42 of the first component 40 moves together with the plunger portion 26 when the plunger portion 26 is depressed or withdrawn relative to the barrel 28. In some embodiments, the first component 40 may include a ridge or groove 44 that is adapted to receive a flange 29 of the proximal end 27 of the plunger portion 26. In some embodiments, the connection may be a snap-fit or other connection that mates with the proximal end 27 of the plunger portion 26 to secure the first component 40 to the plunger portion 26. In some embodiments, the first component 40 may be secured to the plunger portion 26 by friction fit or other methods.

Figure 3:
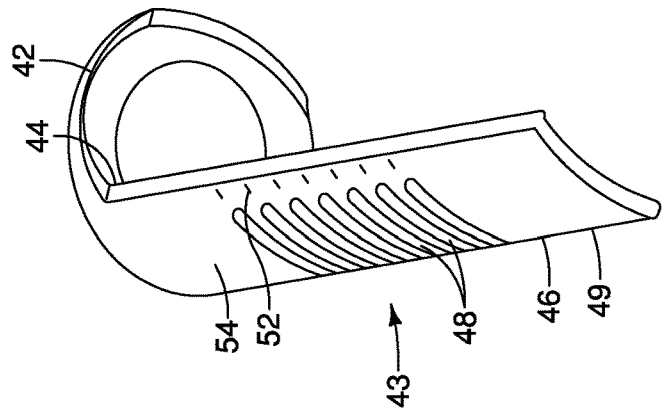
FIG. 3 is a perspective view of an embodiment of a first component of an inflation tool.
Figure 10:
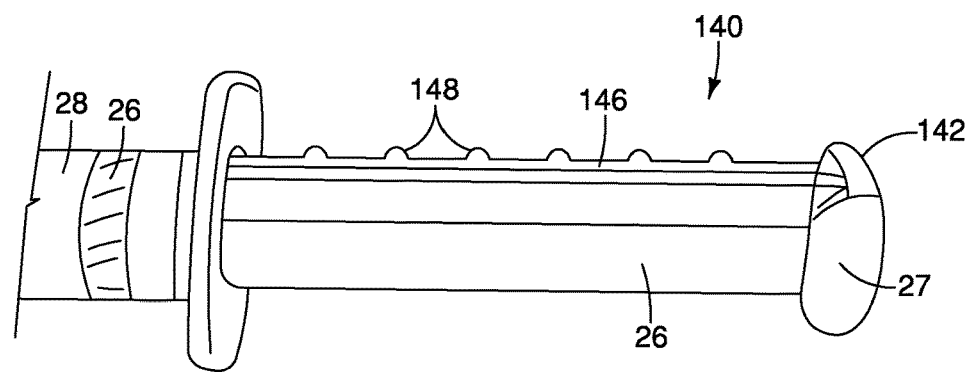
FIG. 10 is a partial view of an inflation system including the inflation tool shown in FIG. 9.
Figure 11:
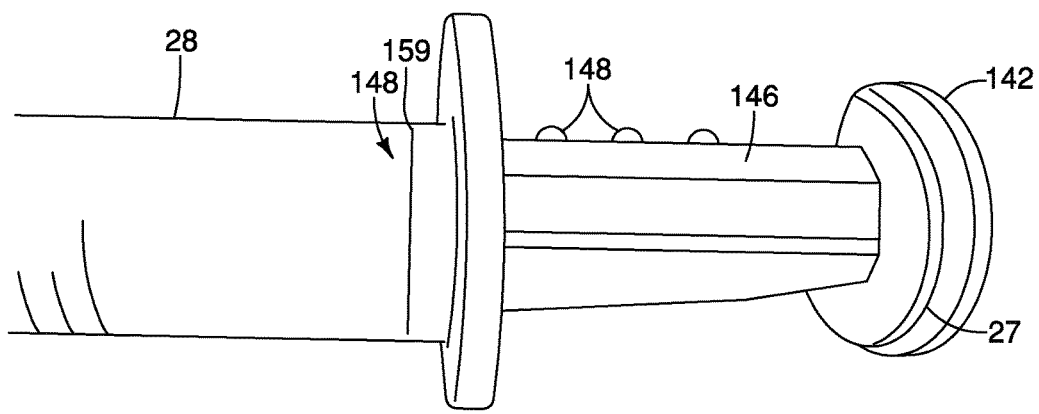
FIG. 11 is a partial view of an inflation system including the inflation tool shown in FIG. 9.

The first component 40 includes a longitudinal arm 46 that extends distally from the proximal end portion 42. The longitudinal arm 46 may be configured to extend along an axis generally parallel to the direction of movement of the first component 40 and the plunger portion 26 of the syringe 16. In some embodiments, the first component 40 may include a first longitudinal arm 46a and a second longitudinal arm 46b as shown in FIG. 2. The first and second longitudinal arms 46a, 46b may be spaced apart by a distance d so that end portions 33 of the flange 32 of the barrel 28 extend through openings 47 between the longitudinal arms 46a, 46b. A distal portion 49 of each longitudinal arm 46 may be unconnected to each other. An embodiment having one longitudinal arm 46 is shown in FIG. 3. The proximal portion 42 may be sized and shaped to fully cover the proximal end 27 of the plunger portion 26 or may partially cover or connect to the plunger portion 26. Each longitudinal arm 46 may include a plurality of positioning members 43 that are spaced apart from each other and are adapted to indicate a position of the first component 40 relative to the barrel 28 of the syringe 16. In some embodiments, the positioning members may comprise a plurality of slots 48 as shown in FIG. 2. The slots 48 may be through going openings or depressions in the longitudinal arm 46. In other embodiments, the positioning members 43 may comprise a plurality of protrusions 148 as described below with reference to FIGS. 9-11.

In some embodiments having more than one longitudinal arm 46, one arm 46 may include slots 48 and the second arm 46 may be free from slots 48. In some embodiments, each arm 46 may include slots 48. Each slot 48 is spaced apart from an adjacent slot 48 along the axis of movement. The plurality of slots are sized and shaped so that a portion of the second component 60 may be received therein as will be described in more detail below. In some embodiments, the first component may include 2, 3, 4 or more longitudinal arms 46 with openings 47 therebetween that allow the first component to move relative to the end portions 33 of the barrel 28. The openings 47 may be sized and shaped to accommodate any size end portions 33 of the barrel 28. Each longitudinal arm 46 may include 2, 3, 4, 5, 6, 7, 8, 9, 10 or more slots 48. The first component 40 may also include areas 56 above and below the slots 48 that are free from slots and may be sized to correspond to a dead volume of air within the inflation system 30 such as the syringe 16 or the balloon catheter 18, so that one inflated size of the balloon member 22 corresponds to one slot 48 as described below.

Each longitudinal arm 46 may be curved to follow the contour of the barrel 28 of the syringe 16, although other shapes are possible. Each longitudinal arm 46 may include a flange 51 on the distal portion 49 that extends outward from the longitudinal arm 46 as shown in the enlarged portion of the first component 40 in FIG. 2A. The flange 51 may be sized and shaped to mate with the second component 60 of the inflation tool 10 as described below. The first component 40 may also include a plurality of markings 52 positioned adjacent to the plurality of slots 48 on an exterior 54 of the first component 40 so that the markings 52 can be viewed by an operator of the inflation system 30. In some embodiments, each slot 48 may include a marking. The markings may be numerical, colored, or both or any type of marking known to one skilled in the art. In some embodiments, the slots 48 and the markings 52 correspond to an inflated diameter of the balloon member 22. Each slot 48 may correspond to an increased inflation diameter of the balloon member 22 from proximal to distal with increasing size. By way of non-limiting example, each slot 48 may increase the balloon member diameter about 0.5 mm, 1 mm, 1.5 mm, 2 mm, 2.5 mm or other increments as the plunger portion 26 is moved distally from one slot 48 to the next more distal slot. In some embodiments, the increments may be linear and in some embodiments the increments may be exponential or other increments.

Figure 4:
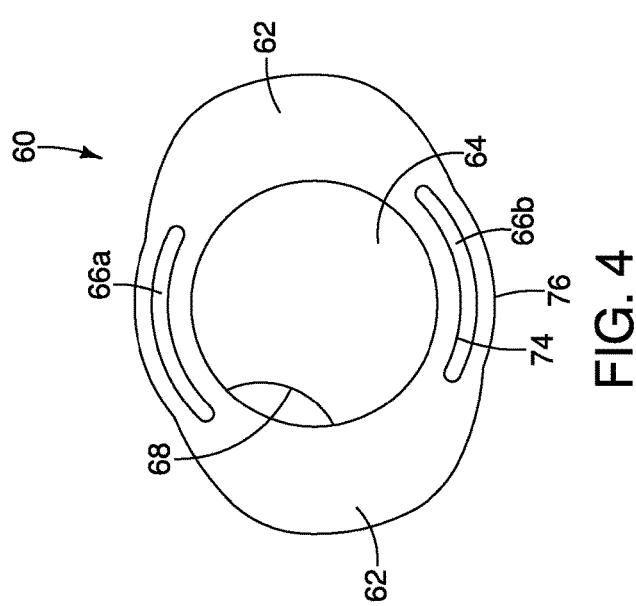
FIG. 4 is a top perspective view of an embodiment of a second component of the inflation tool.

An embodiment of the second component 60 of the inflation tool 10 is shown in FIGS. 4-7. FIG. 4 illustrates a perspective view of the second component 60 from above. The second component 60 may include one or more extensions 62 that are sized and shaped to extend over the end portions 33 of the flange 32 of the syringe barrel 28. The second component 60 also includes a central opening 64 that is sized to receive the plunger portion 26 therethrough. The central opening 64 may be similar in size to or larger than an opening in the barrel 28 into which the plunger portion 26 is inserted.

The second component 60 may also include one or more guide openings 66. The guide openings 66 are sized and shaped to receive a portion of the longitudinal arm 46 of the first component 40 therethrough. By way of non-limiting example, the guide opening 66 may be curved to receive the curved longitudinal arm 46, although other shapes are possible. As shown in FIG. 4, the second component 60 may include two guide openings 66a, 66b to receive two longitudinal arms 46a, 46b. One or both long edges 72 of the guide opening 66 may protrude in an extension 74 that is sized and shaped for releasable insertion of the extension 74 into the one of the slots 48 of the first component 40 as the first component 40 is moved relative to the second component 60. By way of non-limiting example, each guide opening 66 may include the extension 74 to releasably insert into the slots 48 of each longitudinal arm 46 of the first component 40. The slots 48 may have any size or shape to receive any sized and shaped extension 74. By way of non-limiting example, the slots 48 may be rectangular, cylindrical, oval, square or any other shape to receive a matingly shaped extension 74. The extension 74 is configured to removably mate with the slot 48. In some embodiments, one extension 74 may be used even if a plurality of longitudinal arms 46 of the first component 40 is included. The first component 40 may be moved relative to the second component 60 to change the slot 48 into which the extension 74 inserts and thus change the diameter of the balloon member 22. The extension 74 and the slot 48 may be configured so that an audible click is heard by the operator when the extension 74 inserts into the slot 48. An outer edge 76 of the guide opening 66 is adapted to stop the first component 40 from separating from the second component 60 by contacting the flange 51 of the first component 40 when the first component 40 is pulled proximally.

Figure 7:
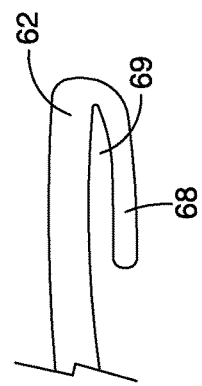
FIG. 7 is a partial side view of the second component shown in FIG. 4.

The second component 60 may also include one or more lower flanges 68. The lower flange 68 is adapted to secure the second component 60 to the flange 32 of the barrel 28. A gap 69 shown in FIG. 7 is formed between the lower flange 68 and the extension 62 that is sized to receive the end portion 33 of the flange 32 of the barrel 28. As shown in the bottom view of FIG. 6, the second component 60 may include two lower flanges 68 to correspondingly mate with two end portions 33 of the barrel 28. In some embodiments, the second component 60 may be rotatably connected or snap-fit connected to the end portions 33 of the barrel 28 of the syringe 26.

Figure 8:
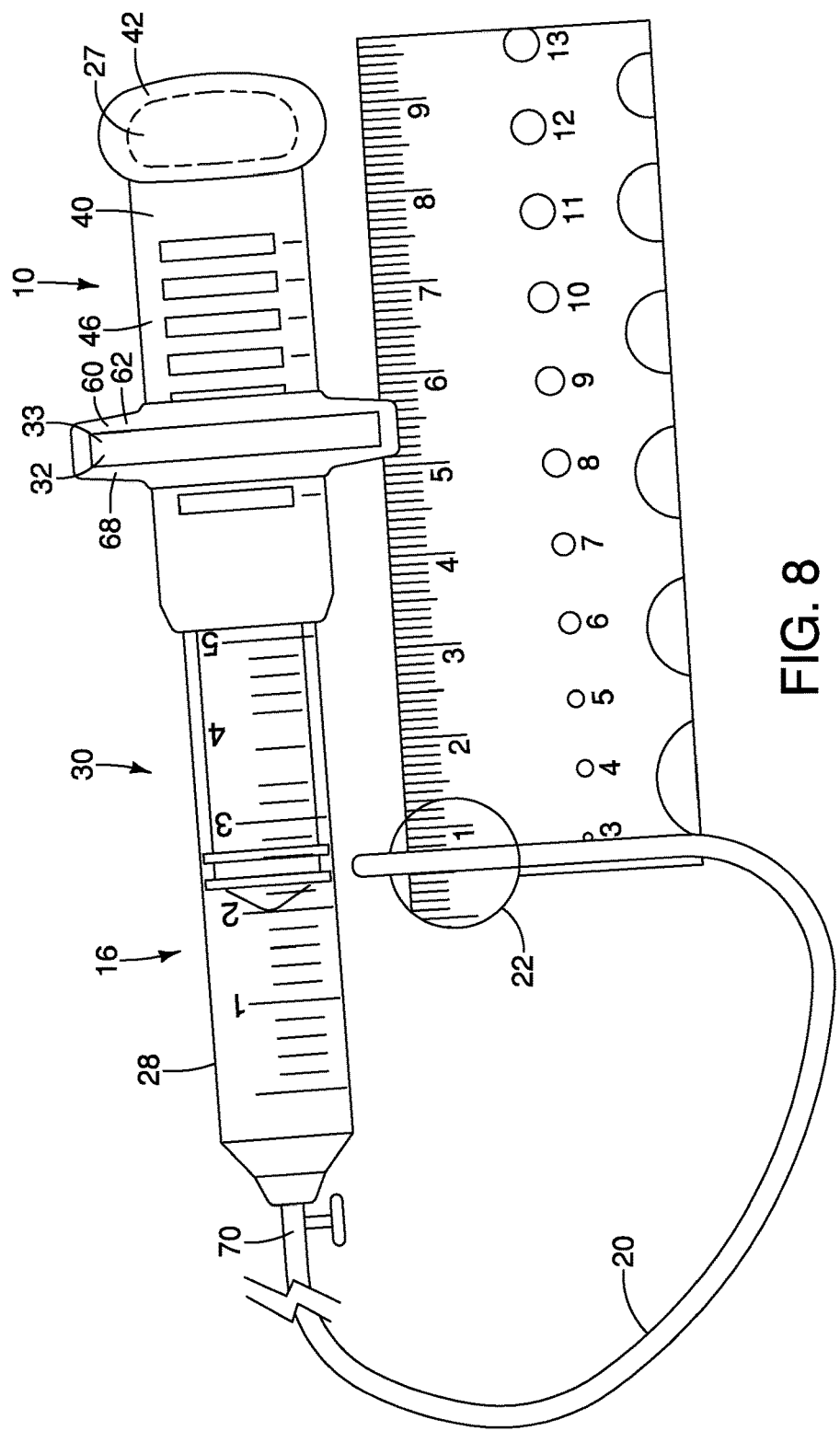
FIG. 8 is a side view of an inflation system in accordance with an embodiment of the present invention.

FIG. 8 illustrates the first component 40 and second component 60 of the inflation tool 10 assembled together with the syringe 16. The second component 60 is positioned on the flange 32 of the barrel 28 of the syringe 16 so that the lower flange 68 and the extension 62 of the second component 60 are positioned over the end portions 33 of the barrel 28. The first component 40 is connected to the plunger portion 26 of the syringe 16. The first component 40 is also movably connected to the second component 60 with the longitudinal arm 46 of the first component 40 inserted through the guide opening 66 of the second component 60. As shown in FIG. 8, the first component 40 and the plunger portion 26 have been moved distally relative to the second component 60 and the barrel 28 so that the balloon member 22 of the inflation system 30 is inflated to the diameter indicted on the marker 52. (Compare to FIG. 1.) The extension 74 of the second component 60 is inserted into the slot 48 of the first component so that the balloon member 22 has the specified inflated diameter. The inflation system 30 may also include a valve or stopcock 70 connected to the syringe 16 and/or the catheter 18 to secure the balloon member 22 at the specified diameter for a procedure. The inflation tool 10 may include a lock to secure the first portion 40 relative to the second portion 60 during a procedure. The inflation tool 10 includes a first component 40. In some embodiments, the inflation tool 10 includes a second component 60 as shown in FIG. 1. The first component 40 may be operably connectable to a plunger portion 26 of the syringe 16. A proximal end portion 42 of the first component 40 connects with a proximal end 27 of the plunger portion 26 so that the first component 40 is movable with the plunger portion 26. Both the first component 40 and the plunger portion 26 move relative to a barrel 28 of the syringe 26. The second component 60 may be operably connectable to a flange 32 on a proximal portion 34 of the barrel 28 of the syringe 16. The first component 40 moves longitudinally relative to the second component 60.

Figure 9:
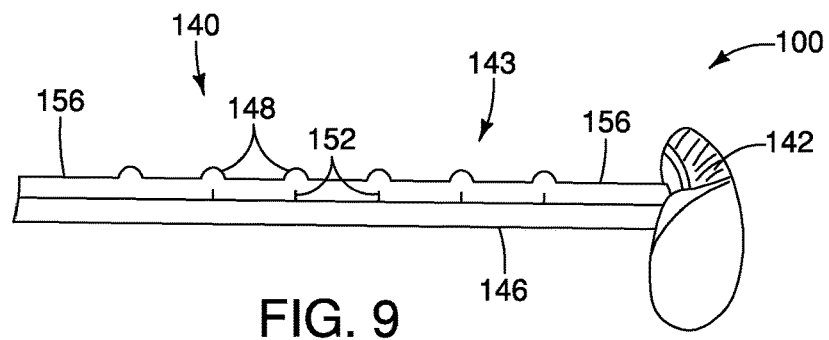
FIG. 9 is a side view of an inflation tool in accordance with an embodiment of the present invention.

FIG. 9 illustrates an embodiment of a first component 140 of an inflation tool 100. The first component 140 includes the proximal end portion 142 that may be sized and shaped to fit over the proximal end 27 of the plunger portion 26 so that the proximal end portion 142 of the first component 140 moves together with the plunger portion 26 when the plunger portion 26 is depressed or withdrawn relative to the barrel 28. In some embodiments, the first component 140 may include a ridge or groove 44 that is adapted to receive a flange 29 of the proximal end 27 of the plunger portion 26. In some embodiments, the connection may be a snap-fit or other connection that mates with the proximal end 27 of the plunger portion 26 to secure the first component 140 to the plunger portion 26. In some embodiments, the first component 140 may be secured to the plunger portion 26 by friction fit or other methods.

The first component 140 includes a longitudinal arm 146 that extends distally from the proximal end portion 142. The longitudinal arm 146 may be configured to extend along an axis generally parallel to the direction of movement of the first component 140 and the plunger portion 26 of the syringe 16. In some embodiments, the first component 140 may include a first longitudinal arm 146a and a second longitudinal arm 146b (not shown) similar to the first and second longitudinal arms 46a, 46b described above. The proximal portion 142 may be sized and shaped to fully cover the proximal end 27 of the plunger portion 26 or may partially cover or connect to the plunger portion 26. As shown in FIG. 9, longitudinal arm 146 includes a plurality of positioning members 143 that are spaced apart from each other and are adapted to indicate a position of the first component 140 relative to the barrel 28 of the syringe 16. As shown, the positioning members 143 comprise a plurality of protrusions 148.

In some embodiments having more than one longitudinal arm 146, one arm 146 may include protrusions 148 and the second arm 146 may be free from protrusions 148. In some embodiments, each arm 146 may include protrusions 148. Each protrusion 148 is spaced apart from an adjacent protrusion 148 along the axis of movement. The plurality of protrusions 148 are sized and shaped so that the protrusions 148 are advanced past a syringe seal 159 on the barrel 29 for each size increment of the balloon member 22. Each longitudinal arm 146 may include 2, 3, 4, 5, 6, 7, 8, 9, 10 or more protrusions 148. The first component 140 may also include areas 156 above and below the protrusions 148 that are free from protrusions and may be sized to correspond to a dead volume of air within the inflation system 30 such as the syringe 16 or the balloon catheter 18, so that one inflated size of the balloon member 22 corresponds to one protrusion 148 as described above.

Each longitudinal arm 146 may be sized and shaped to fit over a portion of the plunger 26 and to fit in the barrel 28 of the syringe 16, although other shapes are possible. The first component 140 may also include a plurality of markings 152 positioned adjacent to the plurality of protrusions 148 on an exterior 154 of the first component 140 so that the markings 152 can be viewed by an operator of the inflation system 30. The markings may be numerical, colored, or both or any type of marking known to one skilled in the art. In some embodiments, the protrusions 148 and the markings 152 correspond to an inflated diameter of the balloon member 22. Each protrusion 148 may correspond to an increased inflation diameter of the balloon member 22 from proximal to distal with increasing size. By way of non-limiting example, each protrusion 148 may increase the balloon member diameter about 0.5 mm, 1 mm, 1.5 mm, 2 mm, 2.5 mm or other increments as the plunger portion 26 is moved distally from one protrusion 148 to the next more distal protrusion. In some embodiments, the increments may be linear and in some embodiments the increments may be exponential or other increments.

The inflation tool 10, 100 is configured to be used with any kind of inflatable member where incremental sizing of the inflatable device is needed. By way of non-limiting example, the inflation tool may be used with extraction balloons for example for sweeping gall stones, calculi, or other obstructions. Exemplary extraction balloons include the DASH Extraction Balloon, ESCORT II Extraction Balloon, TRI-EX Extraction Balloon, FUSION and FUSION QUATRO Extraction Balloon that are available from Cook Medical, Inc. (Bloomington, Ind.) The first component 40, 140 and the second component 60 of the inflation tool 10 may be made from any suitable material. By way of non-limiting example, first component 40, 140 and the second component 60 may be made from a plastic material and injection molded or otherwise molded. The inflation tool may be sized and shaped to fit with any type of syringe used in medical procedures. The inflation tool may also be sized and shaped to be used with any volume displacement device known in the art.

In operation, the inflation tool 10, 100 may be connected to a syringe 16 so that the first component 40, 140 is connected to the plunger portion 26. When included, the second component 60 is connected to the barrel portion 28 of syringe 16. The plunger portion 26 is inserted into the barrel 28 and the longitudinal arm 46 of the first component 40 is positioned through the groove 66 of the second component 60. Alternatively, the first component 140 is positioned on the plunger 26 and the first component 140 is movable with the plunger 26 into the barrel 28 of the syringe 16. The syringe 16 may be coupled to the catheter 18 using a luer connection. The valve 70 may be coupled to the syringe 16 and/or the catheter 18. Excess air may be removed from the system so that the markings 52 on the longitudinal arm 46 accurately reflect the diameter of the balloon member 22. By way of non-limiting example, air or liquid may be used to inflate the balloon member 22.

The balloon member 22 is inserted into the patient's lumen in an uninflated configuration. The position of the balloon member 22 may be visualized endoscopically. The balloon member 22 is inserted into the proper position, for example, distal to an obstruction in the lumen. The balloon member 22 is then inflated using the inflation tool 10. The first component 40, 140 is advanced distally to inflate the balloon member 22. In some embodiments, the first component 40 is advanced distally so that the extension 74 of the second component 60 inserts into a first slot 48a of the first component 40 in a first position of the first component 40. If the balloon member 22 is not of sufficient diameter for the treatment, the first component 40 may be further advanced distally so that the extension 74 of the second component 60 inserts into a second slot 48b of the first component 40 distal to the first slot 48 in a second position of the first component 40. Similarly, the first component 140 may be advanced distally so that a first protrusion 148 is advanced past a syringe seal 159 in a first portion of the first component 140. To further inflate the balloon member 22, the first component 140 may be further advanced distally to so that a second protrusion 148 is advanced past the syringe seal 159 in a second position of the first component 140. The procedure may be repeated to distally advance the first component 40, 140 to a plurality of positions until the desired diameter of the balloon member 22 is achieved. The balloon member 22 may be proximally withdrawn from the lumen to remove the obstruction. The diameter of the balloon member 22 may by increased by distally advancing the first component 40, 140 relative to the syringe barrel 28 and decreased by proximally retracting the first component 40, 140 relative to the syringe barrel 28 during the procedure as needed. The diameter of the balloon member 22 may be held constant once the desired size is reached by closing the valve 70 or by using a lock on the first and second components 40, 60. To deflate the balloon member 22, the plunger portion 27 and the first component 40, 140 are proximally withdrawn. The procedure may be repeated to remove another obstruction.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. An inflation system for inflating a balloon member, the inflation system comprising:
   an inflation tool comprising:
      a first component having a first arm, the first arm extending longitudinally along an axis of movement of the first component, the first arm comprising a first positioning member and a second positioning member, the first positioning member longitudinally spaced apart from the second positioning member, the first component is connectable to a plunger portion of a syringe and is adapted to advance distally for inflation of the balloon member;
   wherein each positioning member corresponds to an inflation increment for the balloon member.

2. The inflation system according to claim 1, wherein the first component further comprises a first marking for the first positioning member and a second marking for the second positioning member.

3. The inflation system according to claim 1, wherein the first component further comprises a proximal end portion sized and shaped to connect to an inflation device of the inflation system.

4. The inflation system according to claim 1, wherein the first component comprises a flange on a distal portion of the first arm.

5. The inflation system according to claim 1, wherein the first component further comprises a second arm spaced apart from the first arm and extending longitudinally along an axis of movement of the first component.

6. The inflation system according to claim 1, further comprising a second component, wherein the second component comprises a flange adapted to secure the second component to the inflation device.

7. An inflation system for inflating a balloon member, the inflation system comprising:
   an inflation tool comprising:
   a first component having a first arm, the first arm extending longitudinally along an axis of movement of the first component, the first arm comprising a first positioning member and a second positioning member, the first positioning member longitudinally spaced apart from the second positioning member, the first component is adapted to advance distally for inflation of the balloon member;
   wherein each positioning member corresponds to an inflation increment for the balloon member; and
   a second component including a first opening and a second opening, the second opening comprising a first extension extending into the second opening, a portion of the first arm extending through the second opening so that the first component is longitudinally movable relative to the second component and the first extension is sized and shaped to mate with the first positioning member in a first position of the first component and a second positioning member in a second position of the first component.

8. The inflation system according to claim 1, further comprising an inflation device, the inflation tool being connectable to the inflation device.

9. The inflation system according to claim 8, wherein the inflation device comprises a syringe including a barrel and a plunger portion, the first component connectable to the plunger and the second component connectable to the barrel.

10. The inflation system according to claim 8, further comprising a catheter and a balloon member operably connected to the inflation device.

11. The inflation system according to claim 8, wherein each positioning member comprises a marking indicating a diameter of the balloon member.

12. The inflation system according to claim 8, wherein the inflation device inflates the balloon member to a first diameter when the first extension mates with the first positioning member and the inflation device inflates the balloon member to a second diameter when the first extension mates with the second positioning member.

13. The inflation system according to claim 8, wherein the first component comprises a plurality of slots, each slot corresponding to a different diameter of the balloon member.

14. The inflation system according to 13, wherein each of the plurality of slots has a marking indicating a diameter of the balloon member, wherein the markings indicate linear or exponential changes in the diameter of the balloon member.

15. The inflation system according to claim 8, wherein the first component is movable distally to increase the diameter of the balloon member and movable proximally to decrease the diameter of the balloon member.

* * * * *